US008304356B2

(12) United States Patent
Fukatani et al.

(10) Patent No.: US 8,304,356 B2
(45) Date of Patent: Nov. 6, 2012

(54) ALUMINOSILICATE GLASS AND COLOR ADAPTING COMPOSITION FOR CERAMICS

(75) Inventors: Yukio Fukatani, Kyoto (JP); Keiji Takahashi, Kyoto (JP); Ryuichi Yoshimoto, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 13/398,885

(22) Filed: Feb. 17, 2012

(65) Prior Publication Data
US 2012/0148750 A1  Jun. 14, 2012

Related U.S. Application Data

(63) Continuation of application No. 12/379,927, filed on Mar. 4, 2009, now abandoned.

(30) Foreign Application Priority Data

Mar. 5, 2008  (JP) ................. 2008-054992

(51) Int. Cl.
*A61C 13/083* (2006.01)
*A61C 13/00* (2006.01)
*C03C 8/22* (2006.01)
*C03C 3/091* (2006.01)

(52) U.S. Cl. ............... 501/16; 501/17; 501/21; 501/66; 106/35; 427/2.29; 264/16; 264/17; 264/18; 264/19; 433/201.1; 433/202.2; 433/203.1

(58) Field of Classification Search .............. 501/16, 501/17, 21, 66; 106/35; 264/16; 65/21.5; 427/2.1, 2.29; 433/218, 201.1, 202.1, 203.1
See application file for complete search history.

(56) References Cited

U.S. PATENT DOCUMENTS

| 4,562,161 | A  |   | 12/1985 | Mennemann et al. |        |
|-----------|----|---|---------|------------------|--------|
| 4,565,791 | A  |   | 1/1986  | Boudot et al.    |        |
| 4,665,039 | A  |   | 5/1987  | Kokubu et al.    |        |
| 6,004,894 | A  | * | 12/1999 | Faust et al.     | 501/17 |
| 6,087,282 | A  | * | 7/2000  | Panzera et al.   | 501/21 |
| 6,120,591 | A  | * | 9/2000  | Brodkin et al.   | 106/35 |
| 6,133,174 | A  |   | 10/2000 | Brodkin et al.   |        |
| 6,500,778 | B1 |   | 12/2002 | Maeda et al.     |        |
| 6,724,094 | B2 |   | 4/2004  | Kosokabe         |        |
| 6,812,175 | B2 |   | 11/2004 | Kawase et al.    |        |
| 6,949,485 | B2 |   | 9/2005  | Nakashima et al. |        |
| 7,341,964 | B2 | * | 3/2008  | Emlemdi          | 501/26 |
| 7,381,258 | B2 | * | 6/2008  | Krumbholz        | 106/35 |
| 7,763,557 | B2 | * | 7/2010  | Baldwin et al.   | 501/14 |
| 2004/0063564 | A1 |   | 4/2004  | Kawai et al.   |        |
| 2005/0215414 | A1 |   | 9/2005  | Kawai          |        |
| 2005/0288165 | A1 | * | 12/2005 | Krumbholz      | 501/6  |
| 2006/0006786 | A1 |   | 1/2006  | Fechner et al. |        |
| 2006/0261503 | A1 |   | 11/2006 | Sago et al.    |        |
| 2008/0020919 | A1 |   | 1/2008  | Murata         |        |

FOREIGN PATENT DOCUMENTS

JP  2007-031180  2/2007

* cited by examiner

*Primary Examiner* — Karl Group
*Assistant Examiner* — Elizabeth A Bolden
(74) *Attorney, Agent, or Firm* — Wenderoth, Lind & Ponack, L.L.P.

(57) ABSTRACT

The present invention relates to a color adapting composition used for coloring and color adapting porcelain for ceramic crown such as dental restorations and prosthetics, and aluminosilicate glass appropriate for using in a color adapting composition. More specifically, a color adapting composition for dental porcelains are prepared by blending two or more kinds of glass frits having different sintering temperatures from each other and an inorganic pigment or a colored glass obtained by previously dispersing inorganic pigments in glass.

4 Claims, No Drawings

ALUMINOSILICATE GLASS AND COLOR ADAPTING COMPOSITION FOR CERAMICS

This application is a continuation of Ser. No. 12/379,927, filed Mar. 4, 2009 now abandoned incorporated herein by reference in its entirety.

TECHNICAL FIELD OF THE INVENTION

The present invention relates to a color adapting composition used for coloring and color adapting ceramic crown porcelain such as dental restorations and prosthetics, and aluminosilicate glass appropriate for using in a color adapting composition.

BACKGROUND ART

Crown restorations providing aesthetics similar to natural teeth include metal ceramic dental restorations and all ceramic dental restorations, both of which are formed with dental porcelain. When these dental restorations are formed, techniques are used for expressing white bands, and stains around cervical portions and proximal surfaces, hair lines, enamel cracks and the like on natural teeth to mimic natural teeth. For this, color-adapting compositions used in ceramic crown porcelain (hereinafter sometimes referred to as "porcelain stain") is used.

Porcelain stains comprise matrix glass and inorganic pigments for coloring.

Generally, techniques for coloring crown restorations to mimic natural teeth include an internal stain technique in which a porcelain stain is used between porcelain portions and an external stain technique in which a porcelain stain is used on the outermost surface of a porcelain portion.

In addition, some of all ceramic crown restorations are formed with various materials such as castable ceramics for a casting process, pressable ceramics for a heat pressing process, CAD/CAM blocks applicable for a CAD/CAM system and the like, and the aesthetic is enhanced by applying a porcelain stain on the surfaces of those crown restorations Usage of porcelain stains is explained below. Firstly, a porcelain stain having an appropriately selected color is placed on a glass plate or a stain palette. Porcelain stains are provided in a form of paste or powder. Therefore, when a porcelain stain is in a form of paste, an appropriate amount of the paste itself is placed on a glass plate or a stain palette, and when a porcelain stain is a form of powder, an appropriate amount of powder is placed on a glass plate or a stain palette and, then, an exclusive liquid is added to knead them into a paste form.

Desired colors may be obtained by blending porcelain stains having different colors at arbitrary ratios. When it is desired to modify application properties or kneading properties for those kneaded to blend colors, a thinning liquid may be appropriately added and kneaded.

The color adapted porcelain stain paste is applied to crown restorations of interest with a brush and the like. The restorations applied with the paste are air-sintered in an optimized sintering schedule by using a porcelain furnace for a dental technology. By sintering, coloring components, which are contained in the porcelain stains, fuse with the crown restorations.

Generally, porcelain stains are properly used for metal ceramic crown restorations and all ceramic crown restorations and, they are called as an internal stain or an external stain depending on parts to be applied.

The reason why properly using as described above is because since metal ceramic crown restorations and all ceramic crown restorations as basements have significantly different linear thermal expansion coefficients from each other, it is needed to use a porcelain stain having a linear thermal expansion coefficient matching with each of crown restorations in order to prevent the porcelain stain from peeling from applied surfaces, cracking, breaking and the like due to an exceeding stress caused by a difference in linear thermal expansion coefficients between the basement and the porcelain stain. Further, it is also the reason that situations for generating stresses are different between inner regions and surface regions of restorations.

Japanese patent No. 4006230 discloses a stain powder and a glazing powder for coloring or glazing full ceramic crowns, but these powders are limited to be used in diopside glass ceramics having a linear thermal expansion coefficient of $4-6 \times 10^{-6} K^{-1}$.

Japanese Patent No. 2847084 discloses a low-temperature sintering stain material (porcelain stain) which contains phosphate glass as a main component, but its composition is limited as 30-80% by weight of $P_2O_3$ and 1-20% by weight of $Al_2O_3$.

[Patent Document 1] Japanese Patent No. 4006230
[Patent Document 2] Japanese Patent No. 2847084

DISCLOSURE OF THE INVENTION

Problem to be Solved by the Invention

The object of the present invention is to provide thermally- and chemically-stable porcelain stain which is widely applicable as an internal stain and an external stain for metal ceramic crown restorations and all ceramic crown restorations.

Specifically, the present invention provides a system capable of producing porcelain stain which exhibits a linear thermal expansion coefficient and a sintering temperature appropriate for ceramic crown porcelain containing conventional colored glass by using matrix glass having a composition in one system.

Means for Solving the Problem

More specifically, the present invention provides aluminosilicate glass containing the following components:
$SiO_2$: 55.0-75.0% by weight,
$B_2O_3$: 5.0-20.0% by weight,
$Al_2O_3$: 5.0-15.0% by weight,
Li2O: 0.5-1.5% by weight,
Na2O: 3.0-8.0% by weight,
K2O: 3.0-8.0% by weight,
CaO: 1.0-5.0% % by weight,
MgO: 0.1-1.0% by weight, and
$Sb_2O_3$: 0.1-1.0% by weight,
and having a sintered temperature of 760-860° C. and a linear thermal expansion coefficient of $6.0 \times 10^{-6} K^{-1}$–$9.0 \times 10^{-6} K^{-1}$ in a range of 25-500° C.

In addition, the present invention provides matrix glass which is a blend of two or more kinds of aluminosilicate glasses for manufacturing porcelain stains, wherein each of the two or more kinds of aluminosilicate glasses is the above mentioned aluminosilicate glass.

The matrix glass according to the present invention may be used to producing porcelain glass having a sintering temperature of 780-860° C. and a linear thermal expansion coefficient of $6.0 \times 10^{-6} K^{-1}$–$9.0 \times 10^{-6} K^{-1}$ in a range of 25-500° C.

It is desirable that a difference in sintering temperatures between the two or more kinds of aluminosilicate glasses constituting the matrix glass according to the present invention is 40° C. or more.

When a blend of two or more kinds of aluminosilicate glasses wherein the difference in sintering temperatures is 40° C. or more is used, regardless of the sintering temperature of colored glass used in porcelain stain, porcelain stain having a sintering temperature lower than the sintering temperature of the basement ceramic crown porcelain may be obtained. Therefore, a sintering process may be carried out at low sintering schedule temperatures at which basement restorations never deform.

The porcelain stain according to the present invention is characterized in that its linear thermal expansion coefficient in a range of 25-500° C. is $6.0\times10^{-6}$ $K^{-1}$–$9.0\times10^{-6}$ $K^{-1}$.

Since the linear thermal expansion coefficient in a range of 25-500° C. for the porcelain stain according to the present invention is adjusted to $6.0\times10^{-6}$ $K^{-1}$–$9.0\times10^{-6}$ $K^{-1}$, a stress caused by a difference in linear thermal expansion coefficients from a variety of restorations constituting basements may be reduced to prevent peeling from applied surfaces, cracking, breaking and the like, regardless of that linear thermal expansion coefficients in a range of 25-500° C. for all ceramic crown restorations and metal ceramic crown restorations constituting a basement is $6.7\times10^{-6}$ $K^{-1}$–$13.0\times10^{-6}$ $K^{-1}$.

Thereby, usage for both of an internal stain and an external stain for metal ceramic crown restorations and all ceramic crown restorations become available.

Further, in the present invention, two or more kinds of aluminosilicate glasses having sintering temperatures different from each other by 40° C. are blended to adjust a sintering temperature of the final porcelain stain to suitable temperatures for a basement crown porcelain regardless of a kind of colored glass.

That is, according to the present invention, for any crown porcelain, a porcelain stain having a desired color can be provided, which can be used in one sintering schedule.

For example, by blending Glass A having a sintering temperature of 760-820° C. and Glass B having a sintering temperature of 800-860° C., a porcelain stain having a sintering temperature of 780-860° C. may be easily produced, even when a colored glass having a sintering temperature over 900° C. is used.

In addition, to the porcelain stain according to the present invention, as a coloring material, an inorganic pigment used for coloring pottery is directly added or a colored glass obtained by previously dispersing inorganic pigments in glass is added.

When a colored glass is used, since inorganic pigments are protected by glass, thermal stability for color development is improved with comparing to a case where inorganic pigments are directly added to a glass frit.

Further, by using finely-ground powder, a porcelain stain may be provided, which has good application properties and shows high stability in fluorescence properties and colors of coloring materials, and which allows making ceramic crown restorations aesthetically closer to natural teeth.

Especially, in order to improve application properties and adaptability to a basement, the maximum particle size of the colored glass is adjusted to 22 μm or smaller. A matrix glass having an average particle size of about 5 μm is used.

Since finely-ground powder is used in a paste-like form, it can be applied very thinly.

EFFECTS OF THE INVENTION

The porcelain stain according to the present invention may be widely applied to from metal ceramic crown porcelain having higher linear thermal expansion coefficients to alumina core crown porcelain having lower linear thermal expansion coefficients.

That is, the porcelain stain according to the present invention is not limited by the linear thermal expansion coefficient of a variety of dental porcelain for basements, and may be applied and sintered without generating peeling or breaking to favorably produce aesthetically excellent crown restorations Since the sintering temperature of the porcelain stain according to the present invention can be adjusted to temperatures lower than sintering temperatures of a variety of dental porcelains, a coloring process can be carried out at low temperatures at which basement restorations never deform.

Since the porcelain stain according to the present invention comprises an aluminosilicate glass as a main component, development of fluorescent materials and color stability of coloring materials are good and it has excellent properties for development of a color of a crown after sintering.

The porcelain stain according to the present invention may be used without any problem even when a content of colored glass is increased in order to heighten a pigment concentration and it is capable of exhibiting various colors.

Further, since the porcelain stain according to the present invention is produced by making a paste with finely-ground powder, it is adaptable with any basements for metal ceramic and all ceramic crown restorations and can be fused in a thin layer.

BEST MODE FOR CARRYING OUT THE INVENTION

Constituents for an aluminosilicate glass used in the porcelain stain according to the present invention will be specifically explained below.

In the above composition of the aluminosilicate glass according to the present invention, the $SiO_2$ content is 55.0-75.0% by weight, preferably 60.0-70.0% by weight. When it is more than 75% by weight, the sintering temperature becomes higher and when it is less than 55% by weight, although the sintering temperature becomes lower, the chemical solubility becomes worse.

In the above composition of the aluminosilicate glass according to the present invention, the $B_2O_3$ content is 5.0-20.0% by weight, preferably 10.0-20.0% by weight. When it is more than 20% by weight, it deviates from a compositional range of the glass formation causing instability, and the chemical solubility becomes worse. On the other hand, when it is less than 5% by weight, the sintering temperature becomes higher.

In the above composition of the aluminosilicate glass according to the present invention, the $Al_2O_3$ content is 5.0-15.0% by weight, preferably 5.0-10.0% by weight. When it is more than 15% by weight, the sintering temperature becomes higher and the fusing properties with basements become worse.

In the above composition of the aluminosilicate glass according to the present invention, the $Li_2O$ content is 0.1-1.5% by weight, preferably 0.5-1.0% by weight. When it is more than 1.5% by weight, the effect of lowering a melting point is enhanced, but the obtained glass is unstable.

In the above composition of the aluminosilicate glass according to the present invention, the $Na_2O$ content is 3.0-8.0% by weight, preferably 4.0-7.0% by weight. When it is more than 8% by weight, the chemical solubility becomes worse and the thermal expansion coefficient increases.

In the above composition of the aluminosilicate glass according to the present invention, the $K_2O$ content is 3.0-8.0% by weight, preferably 4.0-7.0% by weight. When it is more than 8% by weight, the chemical solubility becomes worse and the thermal expansion coefficient increases.

In the above composition of the aluminosilicate glass according to the present invention, it is more preferred that the total content of $Na_2O$ and $K_2O$ is 9.0-14.0% by weight. When the total content of $Na_2O$ and $K_2O$ is more than 14% by weight, the chemical solubility becomes worse and the thermal expansion coefficient increases.

In the above composition of the aluminosilicate glass according to the present invention, the CaO content is 1.0-5.0% by weight, preferably 1.5-3.0% by weight. It is added as carbonate together with $Na_2O$ and $K_2O$ to glass raw materials to assist melting. Further, it is used together with MgO to enhance the chemical solubility.

In the above composition of the aluminosilicate glass according to the present invention, the MgO content is 0.1-1.0% by weight, preferably 0.2-0.8% by weight. It is added as carbonate together with $Na_2O$ and $K_2O$ to glass raw materials to assist melting. Further, it is used together with CaO to enhance the chemical solubility.

In the above composition of the aluminosilicate glass according to the present invention, the $Sb_2O_3$ content is 0.1-1.0% by weight, preferably 0.2-0.8% by weight. It is added to glass in a small amount to assist melting.

In addition, a variety of metal oxides may be added to the aluminosilicate glass other than the above mentioned essential components as far as the linear thermal expansion coefficient in a range of 25° C.-500° C. is maintained to be $6.0 \times 10^{-6} K^{-1}$–$9.0 \times 10^{-6} K^{-1}$.

As raw materials for the aluminosilicate glass according to the present invention, widely and generally used ceramic raw materials may be used. Raw materials are not specifically limited as far as they are the above respective oxides themselves and/or substances which will be converted into the above respective oxides by heating in air. Amounts of respective raw materials are determined by previously calculating glass compositions to be obtained and then they are mixed. In addition, methods for mixing raw materials are not specifically limited but it is preferred that those raw materials are uniformly dispersed.

Glass is formed by fusing the mixed raw materials at least 1200° C. or higher. A method for fusing is not specifically limited as far as the mixed raw materials entirely melt to uniformly become amorphous without causing sublimation of components and the like.

A method for cooling melts is not specifically limited, for example, quenching in water and the like may be carried out.

The glass lumps thus obtained is dried and ground to form glass frit. A method for grinding glass lumps is not specifically limited and a method of classifying into a desired ground particle size.

The porcelain stain according to the present invention contains two or more kinds of the above aluminosilicate glass having different sintering temperatures and a coloring material.

In the present invention, a frit of a colored glass obtained by directly adding coloring inorganic pigments in a glass fit of aluminosilicate glass or by previously dispersing inorganic pigments in glass may be added as coloring material to develop a variety of colors.

Colored glass may be produced by mixing 1-90% by weight of finely-ground pigments and 99-1% by weight of glass frit, by heat-melting the mixture at 1200-1300° C. for about 2 hours to vitrify and by finely grinding the vitrify mixture.

The glass frit used for producing colored glass may be obtained by similar processes for the aluminosilicate glass according to the present invention, and may be those having different compositions from the aluminosilicate glass according to the present invention. There is no limitation for their linear thermal expansion coefficients and sintering temperatures.

Inorganic pigments for coloring pottery are preferably used as pigments used in colored glass, for example, oxides having a Mn—Al composition and a Ca—Sn—Si—Cr composition (pink), a Ti—Cr—Sb composition, a Sn—Al—V composition and a Sn—Si—Al—Ti—V composition (yellow), a Ti—Sb—Si—Cr—Al composition and a Zn—Cr—Fe—Al composition (orange), a Ti—Cr—W composition and a Zn—Fe—Cr—Si—Al—V composition (brown), a Co—Al composition and a Co—Al—Zn composition (blue), a Co—Mn—Cr—Fe composition, a Co—Mn—Cr composition and a Co—Fe—Al—Si composition(black), compositions of $TiO_2$ and $ZrSiO_4$ (white) may be used.

In the present invention, a ground colored glass may be mixed at 10.0-80.0% by weight with respect to 100% by weight of the porcelain stain in order to obtain a desired color.

In addition, it is preferable that at least one of colored glasses or fluorescent materials having an average particle size of 1-5 μm is added and more preferable that both colored glasses and fluorescent materials.

In the present invention, by blending two or more kinds of aluminosilicate glasses having different sintering temperatures from each other by 40° C. or more, a porcelain stain having a sintering temperature of 780-860° C. and a linear thermal expansion coefficient of $6.0 \times 10^{-6} K^{-1}$–$9.0 \times 10^{-6} K^{-1}$ in a range of 25-500° C. may be manufactured regardless of a linear thermal expansion coefficient and a sintering temperature of a colored glass used in the porcelain stain.

The average particle size of aluminosilicate glass used in the porcelain stain according to the present invention is preferably 3-8 μm, more preferably 4-6 μm.

As a method for coloring ceramic crown restorations by using the porcelain stain according to the present invention, conventional methods may be used.

By applying the porcelain stain according to the present invention as an internal stain or an external stain to all ceramic crown restorations formed by ordinary methods or metal ceramic crown restorations restored by using an alumina core or a zircornia core and by sintering it, it becomes possible to express white bands, stains around cervical portions and proximal surfaces, hair lines, enamel cracks and the like on natural teeth.

EXAMPLES

The present invention will be further explained with referring to Examples and Comparative Examples, but the present invention is never limited to these Examples and Comparative Examples.

Evaluation methods for sintering temperatures, thermal expansion coefficients and fusing properties of compositions, porcelains and the like in the Examples and Comparative Examples are shown below.
(Evaluation of Sintering Temperature)

Each of the porcelain stains in Examples and Comparative Examples was kneaded with distilled water and the kneaded material was filled into a button-shaped silicone mold (3 mm×10 mm diameter). Then, the button-like mold was vibrated with a ultrasonic vibrator Ceramosonic Condenser (manufactured by Shofu Inc.), a building-up spatula or the like to percolate water from the kneaded material in a wet state in order to increase the powder tap density (condensation), and the percolated water was absorbed with tissue paper and the like. A molded form was obtained by repeating condensation and absorption.

The obtained molded form was removed form the silicone mold and it was air-sintered in an electrical vacuum furnace for porcelain Single Mat (manufactured by Shofu Inc.) to evaluate the sintering temperature of the respective stains.

In the present invention, the term "sintering temperature" means a temperature at which the surface of the molded form becomes smooth and glossy, that is, a self-glazing state. More specifically, the above molded form is placed in a furnace previously heated at 600° C. and it is air-sintered by raising a temperature from 600° C. to an appropriate, peak temperature at a heating rate of 50° C./min. At a time when a temperature reaches to the peak temperature, it is rapidly cooled at room temperature and its sintered state is observed. When the surface is in a biscuit-like rough state, and sharp edges of the molded form remain, it is air-sintered again at a raised temperature by 10° C. The sintered state is observed. The sintering schedule temperature at which the sintered material becomes uniformly translucent and the surface becomes slightly glossy is defined as a sintering temperature.

(Evaluation of Thermal Expansion Coefficient)

Each of the porcelain stains in Examples and Comparative Examples was kneaded with distilled water and the kneaded material was filled into a bar-shaped silicone mold (6×6×25 mm). A molded form was obtained by repeating condensation and absorption.

The obtained molded form was removed from the silicone mold and it was air-sintered twice in an electrical vacuum furnace for porcelain Single Mat (manufactured by Shofu Inc.). In either of the first and the second sintering, it was raised to approximately the final sintering temperature determined for the respective compositions by using the above mentioned method for evaluating sintering temperatures.

A specimen prepared by cutting the both ends of the twice sintered material to form parallel surfaces and shaped into a size of 20×5×5 mm was used as a test sample and its linear thermal expansion coefficient in a range of 25-500° C. was measured with a thermal dilatometer TMA8140C (manufactured by Rigaku Corporation).

(Evaluation of Fusing Property)

Each of the porcelain stains in Examples and Comparative Examples was converted into a paste by adding an exclusive liquid to endow powder with an application property. The obtained paste was applied on a dental restoration formed by using various dental porcelains and they were sintered.

In this evaluation, a single crown formed by building up a dental porcelain for metal bonding which has a linear thermal expansion coefficient of $13.0 \times 10^6$ $K^{-1}$ (manufactured by Shofu Inc.) on a metal core, a single crown formed by building up a dental porcelain for alumina copings which has a linear thermal expansion coefficient of $6.7 \times 10^{-6} K^{-1}$ (manufactured by Shofu Inc.) on an alumina core (manufactured by Nobel Biocare) and a single crown formed by building up a dental porcelain for zircornia copings which has a linear thermal expansion coefficient of $9.4 \times 10^{-6} K^{-1}$ (manufactured by Shofu Inc.) on a zirconia core (manufactured by Nobel Biocare).

Single crowns were formed by sintering at 940° C. regarding the dental porcelain for metal bond and at 920° C. regarding the dental porcelains for alumina copings and zirconia copings.

If the porcelain stains are fused at sintering schedule temperatures not lower than the sintering temperature of the dental restoration which is a basement, the basements will deform. Therefore, in this evaluation, the sintering temperature for the porcelain stain was adjusted to 850° C.

The above paste was applied on each of single crowns and they were placed in an electrical vacuum furnace for porcelain Single Mat (manufactured by Shofu Inc.), which was previously heated at 600° C. Then, they were air-sintered by raising a temperature from 600° C. to a peak temperature of 850° C. at a heating rate of 50° C./min. At a time when a temperature reaches to the peak temperature, it is rapidly removed from the furnace to cool at room temperature.

After cooling to room temperature, when neither of cracks, breaks, peelings, clouds and the like was visually observed on porcelain surfaces and a good adaptability with the basement was obtained, it is signed with a symbol "○", and when cracks, breaks, peelings, clouds and the like were visually observed, it is signed with a symbol "×".

Additionally, since the exclusive liquid use to make a paste burns out at around 500° C., it never affects evaluation for fusing.

(Evaluation of Composition)

Specimens were prepared by pressing the respective porcelain stains in Examples and Comparative Examples into a special holder with a pressing machine (at a pressure of 20 tons) and quantitative analysis was performed on a fluorescent X-ray analyzer ZSX100 e (manufactured by Rigaku Corporation).

With an assumption that all elements exist in a form of oxides, composition ratios of oxides were calculated based on the obtained elemental analysis values.

(Evaluation of Chemical Solubility)

Each of the porcelain stains in Examples and Comparative Examples was kneaded with distilled water and the kneaded material was filled into a disc-shaped silicone mold (12 mm in diameter, 2 mm in depth). Molded forms were obtained by repeating condensation and absorption.

The obtained molded forms were removed from the silicone mold and it was air-sintered in an electrical vacuum furnace for porcelain Single Mat (manufactured by Shofu Inc.) to prepare 10 samples. Both surfaces for these samples were ground to form planes followed by air-sintering again.

According to the procedures of ISO6872, these samples were tested for solubility by using an extractor with a reflux condenser. When this test result was lower than the value defined in the ISO standard (the maximum eluted mass: 100 $\mu g\ cm^{-2}$), it was judged as "○". To the contrary, when the test result was higher than the value, it was judged as "×".

Examples 1-5

Comparative Examples 1-3

Adjusting and blending were performed to manufacture Glasses 1-5 (Examples 1-5) and Glasses 6-8 (Comparative Examples 1-3) so as to have oxide compositions shown in Table 1.

Results of sintering temperatures, linear thermal expansion coefficients in a range of 25-500° C., fusing properties and chemical solubility for the obtained glasses are shown in Table 2.

TABLE 1

|  | SiO$_2$ | B$_2$O$_3$ | Al$_2$O$_3$ | Li$_2$O | Na$_2$O | K$_2$O | CaO | MgO | Sb$_2$O$_3$ | P$_2$O$_5$ |
|---|---|---|---|---|---|---|---|---|---|---|
| Glass 1 | 67.8 | 12.5 | 7.2 | 1.0 | 4.8 | 4.4 | 1.3 | 0.5 | 0.5 | 0.0 |
| Glass 2 | 65.0 | 9.3 | 7.6 | 1.0 | 5.6 | 5.7 | 5.0 | 0.5 | 0.3 | 0.0 |
| Glass 3 | 63.4 | 11.0 | 8.2 | 0.5 | 7.0 | 5.4 | 3.4 | 0.7 | 0.4 | 0.0 |
| Glass 4 | 69.8 | 9.5 | 7.4 | 1.0 | 4.7 | 4.7 | 2.4 | 0.1 | 0.4 | 0.0 |
| Glass 5 | 61.6 | 16.7 | 6.8 | 0.8 | 6.2 | 5.0 | 2.3 | 0.1 | 0.5 | 0.0 |
| Glass 6 | 55.2 | 6.0 | 17.3 | 0.5 | 7.6 | 7.9 | 5.2 | 0.3 | 0.0 | 0.0 |
| Glass 7 | 56.5 | 5.8 | 7.0 | 0.0 | 21.8 | 1.1 | 2.1 | 3.5 | 0.0 | 2.2 |
| Glass 8 | 62.2 | 0.0 | 15.4 | 0.0 | 6.9 | 13.9 | 1.0 | 0.6 | 0.0 | 0.0 |

TABLE 2

|  | Sintering temperature (° C.) | Linear thermal expansion coefficient (×10$^{-6}$ K$^{-1}$) | Fusing properties | Chemical solubility |
|---|---|---|---|---|
| Glass 1 | 840 | 6.1 | ○ | ○ |
| Glass 2 | 820 | 6.9 | ○ | ○ |
| Glass 3 | 840 | 6.8 | ○ | ○ |
| Glass 4 | 820 | 5.8 | ○ | ○ |
| Glass 5 | 780 | 6.9 | ○ | ○ |
| Glass 6 | 880 | 9.1 | ○ | ○ |
| Glass 7 | 780 | 11.1 | X | ○ |
| Glass 8 | 880 | 15.0 | X | ○ |

Glasses 1-5 in Examples 1-5 have sintering temperatures and linear thermal expansion coefficients within respective desired ranges. On the other hand, Glasses 6-8 in Comparative Examples 1-3 did not satisfy both sintering temperature and linear thermal expansion coefficient.

In addition, the glasses of Examples 1-5 could fuse well but the Glasses 7 and 8 could not fuse well because their linear thermal expansion coefficients were high.

Additionally, all the glasses satisfied chemical solubility.

Example 6-11

Comparative Example 4-6

The porcelain stains 1-6 having compositions shown in Table 4 (Example 6-11) were manufactured by blending the Glass 1 (Example 1) having a sintering temperature of 840° C., the Glass 5 (Example 5) having a sintering temperature of 780° C. and the colored glass shown in Table 3.

In addition, the porcelain stains 7-8 having compositions shown in Table 4 (Comparative Example 4-6) were manufactured by blending the Glass 6 having a sintering temperature of 880° C. (Comparative Example 1) and the colored glass shown in Table 3.

Results of sintering temperatures, linear thermal expansion coefficients in a range of 25-500° C. and fusing properties for the obtained porcelain stains are shown in Table 5.

TABLE 3

|  | Color | Sintering temperature (° C.) | Linear thermal expansion coefficient (×10$^{-6}$ K$^{-1}$) |
|---|---|---|---|
| Colored glass A | Yellow | 980 | 7.4 |
| Colored glass B | Pink | 1000 | 8.0 |
| Colored glass C | Brown | 900 | 8.4 |
| Colored glass D | Black | 900 | 8.7 |

TABLE 4

|  | Glass 1 | Glass 5 | Glass 6 | Colored glass A | Colored glass B | Colored glass C | Colored glass D |
|---|---|---|---|---|---|---|---|
| Stain 1 | 40 | 35.9 |  | 24 | 0.1 |  |  |
| Stain 2 | 81 | 5 |  | 1 | 13 |  |  |
| Stain 3 | 0.5 | 29 |  |  |  | 67.5 | 3 |
| Stain 4 | 60 | 23 |  | 16 | 1 |  |  |
| Stain 5 | 1 | 45 |  | 24 |  | 30 |  |
| Stain 6 | 80 | 5 |  |  | 12 | 3 |  |
| Stain 7 |  |  | 60 | 40 |  |  |  |
| Stain 8 |  |  | 85 |  | 15 |  |  |
| Stain 9 |  |  | 30 |  |  | 70 |  |

TABLE 5

|  | Sintering temperature (° C.) | Linear thermal expansion coefficient (×10$^{-6}$K$^{-1}$) | Chemical solubility |
|---|---|---|---|
| Stain 1 | 850 | 7.2 | ○ |
| Stain 2 | 850 | 6.4 | ○ |
| Stain 3 | 850 | 8.2 | ○ |
| Stain 4 | 850 | 6.3 | ○ |
| Stain 5 | 850 | 7.8 | ○ |
| Stain 6 | 850 | 6.2 | ○ |
| Stain 7 | 900 | 8.8 | X |
| Stain 8 | 920 | 8.9 | X |
| Stain 9 | 920 | 8.7 | X |

Although the colored glass having a sintering temperature greatly deviating from the desired range (the sintering temperature: 900-1000° C.) was used, by blending the Glass 1 and Glass 5 according to the present invention, a porcelain stain having a desired sintering temperature (780-860° C.) and a desired linear thermal expansion coefficient in a range of 25-500° C. (6.0×10$^{-6}$ K$^{-1}$–9.0×10$^{-6}$ K$^{-1}$) could be manufactured. Further, its fusing property was also good.

According to the present invention, by using two or more kinds of aluminosilicate glasses having different sintering temperatures from each other, a porcelain stain may be manufactured which is capable of being sintered at temperatures lower than the sintering temperature of a dental porcelain to be used for a basement and capable of being blended with various colored glasses.

In addition, since the linear thermal expansion coefficient is adjusted to be low, it can be used as internal stains and external stains for metal ceramic crown restorations and all ceramic crown restorations.

Further, since finely-ground powder is used, a porcelain stain has good application properties and high adaptability with a basement.

What we claimed:

1. A method for manufacturing a porcelain stain, comprising:
    a Step 1 of forming aluminosilicate glass A having a sintering temperature of 760-820 ° C. and a linear thermal expansion coefficient of 6.0×10$^{-6}$ K$^{-1}$–9.0×10$^{-6}$ K$^{-1}$ in a range of 25-500 °C. by fusing a mixed raw material at least 1200 °C. or higher, wherein the mixed raw material comprises the following components:

$SiO_2$: 55.0-75.0% by weight,
$B_2O_3$: 5.0-20.0% by weight,
$Al_2O_3$: 5.0-15.0% by weight,
$Li_2O$ : 0.5-1.5% by weight,
$Na_2O$ : 3.0-8.0% by weight,
$K_2O$ : 3.0-8.0% by weight,
$CaO$ : 1.0-5.0% by weight,
$MgO$ : 0.1-1.0% by weight,
$Sb_2O_3$: 0.1-1.0% by weight;

a Step 2 of obtaining a glass lump by cooling a melt of the aluminosilicate glass A, and drying and grinding the glass lump to form glass frit having an average particle size of 3-8 μm;

a Step 3 of forming aluminosilicate glass B having a sintering temperature of 800-860 °C. which is different from by 40° C. or more than that of the aluminosilicate glass A and a linear thermal expansion coefficient of $6.0\times10^{-6}\,K^{-1}$–$9.0\times10^{-6}\,K^{-1}$ in a range of 25-500 °C. by fusing another mixed raw material at least 1200 °C. or higher, wherein the mixed raw material comprises the following components:

$SiO_2$: 55.0-75.0% by weight,
$B_2O_3$: 5.0-20.0% by weight,
$Al_2O_3$: 5.0-15.0% by weight,
$Li_2O$ : 0.5-1.5% by weight,
$Na_2O$ : 3.0-8.0% by weight,
$K_2O$ : 3.0-8.0% by weight,
$CaO$ : 1.0-5.0% by weight,
$MgO$ : 0.1-1.0% by weight,
$Sb_2O_3$: 0.1-1.0% by weight;

a Step 4 of obtaining a glass lump by cooling a melt of the aluminosilicate glass B, drying and grinding the glass lump to form glass frit having an average particle size of 3-8 μm; and a Step 5 of mixing the glass frit obtained in Step 2, the glass frit obtained in Step 4 and a coloring material to manufacture a porcelain stain having a sintering temperature of 760-860 °C. and a linear thermal expansion coefficient of $6.0\times10^{-6}\,K^{-1}$–$9.0\times10^{-6}\,K^{-1}$ in a range of 25-500 °C.

2. A method for coloring ceramic crown restorations by applying the porcelain stain obtained by the method of claim 1 as an internal stain or an external stain to ceramic crown restorations or metal ceramic crown restorations restored by using an alumina core or a zircornia core and by sintering it to express white bands, stains around cervical portions and proximal surfaces, hair lines, enamel cracks on natural teeth.

3. A method for manufacturing a porcelain stain, comprising:

a Step 1 of forming aluminosilicate glass A having a sintering temperature of 760-820 °C. and a linear thermal expansion coefficient of $6.0\times10^{-6}\,K^{-1}$–$9.0\times10^{-6}\,K^{-1}$ in a range of 25-500 °C. by fusing a mixed raw material at least 1200 °C. or higher, wherein the mixed raw material comprising the following components:

$SiO_2$: 55.0-75.0% by weight,
$B_2O_3$: 5.0-20.0% by weight,
$Al_2O_3$: 5.0-15.0% by weight,
$Li_2O$ : 0.5-1.5% by weight,
$Na_2O$ : 3.0-8.0% by weight,
$K_2O$ : 3.0-8.0% by weight,
$CaO$ : 1.0-5.0% by weight,
$MgO$ : 0.1-1.0% by weight,
$Sb_2O_3$: 0.1-1.0% by weight;

a Step 2 of obtaining a glass lump by cooling a melt of the aluminosilicate glass A, drying and grinding the glass lump to form glass frit having an average particle size of 3-8 μm;

a Step 3 of forming aluminosilicate glass B having a sintering temperature of 800-860 °C. which is different from by 40° C. or more than that of the aluminosilicate glass A and a linear thermal expansion coefficient of $6.0\times10^{-6}\,K^{-1}$–$9.0\times10^{-6}\,K^{-1}$ in a range of 25-500 °C. by fusing another mixed raw material at least 1200 °C. or higher, wherein the mixed raw material comprising the following components:

$SiO_2$: 55.0-75.0% by weight,
$B_2O_3$: 5.0-20.0% by weight,
$Al_2O_3$: 5.0-15.0% by weight,
$Li_2O$ : 0.5-1.5% by weight,
$Na_2O$ : 3.0-8.0% by weight,
$K_2O$ : 3.0-8.0% by weight,
$CaO$ : 1.0-5.0% by weight,
$MgO$ : 0.1-1.0% by weight,
$Sb_2O_3$: 0.1-1.0% by weight;

a Step 4 of obtaining a glass lump by cooling a melt of the aluminosilicate glass B, drying and grinding the glass lump to form glass frit having an average particle size of 3-8 μm;

a Step 5-1 of mixing the glass frit obtained in Step 2, the glass frit obtained in Step 4 and a coloring material to form a colored glass frit;

a Step 5-2 of mixing the glass frit obtained in Step 2 and the glass frit obtained in Step 4 to form a glass frit; and a Step 6 of mixing the colored glass frit obtained in Step 5-1 and the glass frit obtained in Step 5-2 to manufacture a porcelain stain having a sintering temperature of 780-860 °C. and a linear thermal expansion coefficient of $6.0\times10^{-6}\,K^{-1}$–$9.0\times10^{-6}\,K^{-1}$ in a range of 25-500 °C.

4. A method for coloring ceramic crown restorations by applying the porcelain stain obtained by the method of claim 3 as an internal stain or an external stain to ceramic crown restorations or metal ceramic crown restorations restored by using an alumina core or a zircornia core and by sintering it to express white bands, stains around cervical portions and proximal surfaces, hair lines, enamel cracks on natural teeth.

* * * * *